(12) United States Patent
Bonnet et al.

(10) Patent No.: US 7,396,961 B2
(45) Date of Patent: Jul. 8, 2008

(54) PROCESS FOR CATALYTICALLY DECOMPOSING ORGANIC HYDROPEROXIDES

(75) Inventors: Didier Bonnet, Lyons (FR); Eric Fache, Caluire (FR); Aline Seigneurin, Le Chesnay (FR)

(73) Assignee: Rhodia Polyamide Intermediates, Saint_Fons (FR)

( * ) Notice: Subject to any disclaimer, the term of this patent is extended or adjusted under 35 U.S.C. 154(b) by 0 days.

(21) Appl. No.: 11/336,008

(22) Filed: Jan. 20, 2006

(65) Prior Publication Data

US 2007/0129575 A1    Jun. 7, 2007

Related U.S. Application Data

(63) Continuation of application No. 10/493,876, filed on Aug. 18, 2004, now abandoned.

(51) Int. Cl.
*C07C 45/53* (2006.01)
*C07C 37/08* (2006.01)

(52) U.S. Cl. .................. 568/338; 568/342; 568/354; 568/361; 568/385; 568/798; 568/820

(58) Field of Classification Search ............... None
See application file for complete search history.

(56) References Cited

U.S. PATENT DOCUMENTS

| | | | |
|---|---|---|---|
| 2,851,496 A | 9/1958 | Cates, Jr. .................... | 568/342 |
| 3,927,105 A | 12/1975 | Brunie et al. | |
| 4,551,553 A | 11/1985 | Taylor et al. ............... | 588/409 |
| 4,918,238 A | 4/1990 | Costantini et al. | |
| 5,672,778 A | 9/1997 | Lyons et al. | |
| 5,728,890 A | 3/1998 | Hamamoto et al. ........ | 568/361 |
| 2003/0097025 A1 | 5/2003 | Clark et al. | |

FOREIGN PATENT DOCUMENTS

| | | |
|---|---|---|
| DE | 198 49 593 A1 | 5/2000 |
| EP | 0 270 468 B1 | 7/1991 |
| EP | 0 331 590 B1 | 4/1993 |
| FR | 1 580 206 | 9/1969 |
| FR | 2 087 375 | 12/1971 |
| FR | 2 744 719 A | 8/1997 |
| WO | WO 01/44153 A | 6/2001 |

OTHER PUBLICATIONS

C. B. Hansen et al., "Metalloporphyrins as catalysts in the decomposition of cyclohexyl hydroperoxide", *Catalysis Letters*, 20 (1993), pp. 259-364.
C. A. Tolman et al., "Catalytic Conversion of Cyclohexylhydroperoxide to Cyclohexanone and Cyclohexanol", *Journal of Molecular Catalysis*, 48(1988), pp. 129-148.
L. Saussin et al., "Cobalt(III) Alkylperoxy Complexes. Synthesis, X-ray Structure, and Role in the Catalytic Decomposition of Alkyl Hydroperoxides and in the Hydroxylation of Hydrocarbons", *Journal of American Chemical Society* (1985), 107, pp. 3534-3540.
C. B. Hansen et al., "Anchored manganese and ruthenium porphyrins as catalysts in the decomposition of cyclohexyl hydroperoxide," *Journal of Molecular Catalysis*, 79 (1993), pp. 153-163.
T. P. Wijesekera et al., "Perfluoroalkylporphyrin complexes as active catalysts for the reaction of isobutane with oxygen and the decomposition of tert-butyl hydroperoxide", *Catalysis Letters* 36(1996), pp. 69-73.

*Primary Examiner*—Sikarl A Witherspoon
(74) *Attorney, Agent, or Firm*—Buchanan, Ingersoll & Rooney, PC

(57) ABSTRACT

The present invention relates to a process for decomposing organic hydroperoxides in the presence of a catalyst. It provides a process for decomposing organic hydroperoxides in the presence of a catalyst into a mixture of alcohols and ketones, in which the catalyst comprises at least one ruthenium-based catalytically active metallic element incorporated into a solid support chosen from the group comprising metal oxides and carbon blacks, such as the carbon blacks obtained by the pyrolysis of organic compounds. The process of the invention is especially useful in the decomposition of important chemical intermediates such as cyclohexyl hydroperoxide.

11 Claims, No Drawings

PROCESS FOR CATALYTICALLY DECOMPOSING ORGANIC HYDROPEROXIDES

This application is a continuation of U.S. application Ser. No. 10/493,876, filed on Aug. 18, 2004 now abandoned.

The present invention relates to a process for decomposing organic hydroperoxides in the presence of a catalyst.

Organic hydroperoxides are important inter-mediates in the preparation of alcohols, ketones and acids, and are themselves often used as raw materials in organic synthesis.

Among these organic hydroperoxides, cyclohexyl hydroperoxide is prepared by the oxidation of cyclohexane. Catalytic decomposition of the latter leads to cyclohexanone and cyclohexanol. The latter two compounds may be converted into adipic acid by oxidation. Adipic acid is an important chemical inter-mediate used in the manufacture of many polymers, such as polyamides and polyurethanes for example. This compound may have many other applications.

The decomposition of organic hydroperoxides and especially of cyclohexyl hydroperoxide (CHHPO) may firstly be carried out by homogeneous catalysis, that is to say in the presence of a catalyst dissolved in the reaction mixture. Thus, patent FR-A-1 580 206 describes the oxidation of a cycloalkane in liquid phase followed by heating of the cycloalkyl hydroperoxide solution in the cycloalkane thus obtained, in the presence of a soluble chromium derivative as catalyst. Likewise, the article from the Journal of Molecular Catalysis (1988), 48, pages 129 to 148 describes the use of organic salts, such as cobalt octanoate or of complexes, dissolved in the organic liquid phase in which the reaction takes place.

However, the use of such inexpensive salts has drawbacks since these catalysts very rapidly become deactivated, causing them to precipitate in the mixture.

To remedy these problems, more complex catalytic systems have been recommended, such as complexes between a metal and porphyrins or phthalocyanines. Such systems have, for example, been described in the patent U.S. Pat. No. 5,672,778 and the articles published in Catalysis Letters 20, 1993, 359-364 or 36, 1996, 69-73. Complexes based on cobalt and on similar ligands have also been described in the article published in Journal of the American Chemical Society (1985), 107, pages 3534 to 3540.

It has also been proposed, for example in European Patent 270 468, to use ruthenium and a coordinate based on bis (pyridyl-2-imino)-1,3-isoindoline.

These catalytic systems have drawbacks, especially associated with their stability (oxidation resistance) and their complexity, making them expensive.

It has also been proposed to decompose the hydroperoxide by heterogeneous catalysis, that is to say in the presence of a catalyst not dissolved in the reaction mixture. However, these catalysts often have a rapidly decreasing activity, this loss of activity being due, for example, to elution of the catalytic phase.

Moreover, it has also been proposed to use catalysts which make it possible, simultaneously with the decomposition of the hydroperoxide into an alcohol and/or a ketone, to oxidize the hydrocarbon used as solvent, thus allowing the total conversion yield from hydrocarbon to alcohol and ketone to be improved. This oxidation is called in the present technical field "an oxygen transfer". It consists in transferring one of the oxygen atoms of the hydroperoxide to the hydro-carbon in order to obtain the corresponding alcohol. European Patent 0331590 describes the use of a homogeneous catalyst based on osmium complexes, which is used to obtain an oxygen transfer of around 40%.

The object of the present invention is to provide a novel heterogeneous catalytic system which is economically beneficial and makes it possible in particular to obtain a high level of oxygen transfer.

More specifically, it provides a process for decomposing organic hydroperoxides in the presence of a catalyst into a mixture of alcohols and ketones, in which the catalyst comprises at least one ruthenium-based catalytically active metallic element incorporated into a solid support chosen from the group comprising metal oxides and carbon blacks, such as the carbon blacks obtained by pyrolysis of organic compounds.

The catalyst of the invention is a heterogeneous catalyst that can be obtained by any standard technique for manufacturing catalysts referred to as supported catalysts. Thus, the term "incorporated" used above covers all forms of linking between the support and the ruthenium compound(s) or complex(es). Thus, this term covers both absorption of the ruthenium compounds on a support and coprecipitation of the ruthenium and a precursor of the support. The ruthenium may be simply deposited on the surface of the support, especially the surface of at least certain pores of the support, or otherwise it may be linked to the said support via electronic bonds.

The suitable supports for the invention advantageously have a high specific surface area and are oxidation resistant. Metal oxides having a specific surface area of greater than 10 $m^2/g$, advantageously greater than 100 $m^2/g$, are the preferred supports of the invention.

As examples of suitable supports for the invention, mention may be made of aluminas, rare-earth oxides, such as cerium or lanthanum oxide, zirconium oxide and magnesium oxide, silica and various carbon blacks preferably having a high specific surface area, such as, for example, acetylene blacks.

The catalyst of the invention may also include other metallic elements for improving or doping the catalytic activity of the ruthenium. As metallic elements suitable to act as dopants, mention may be made of the transition metals such as those belonging to Groups 1b, 2b, 3b, 4b, 5b, 6b, 7b and 8 of the Periodic Table of Elements as published in *Handbook of Chemistry and Physics*, $66^{th}$ edition (1985/1986) by The Chemical Rubber Co.

Mention may more particularly be made of titanium, zirconium, vanadium, niobium, tantalum, chromium, molybdenum, tungsten, manganese, rhenium, iron, cobalt, nickel, rhodium, palladium, platinum, iridium, osmium, copper, silver, gold and rare-earth metals such as lanthanum and cerium.

The decomposition reaction of the invention is carried out in liquid phase, the concentration of the hydroperoxide being between 0.1 and 80% by weight in the reaction mixture. Advantageously, this concentration is between 0.5 and 20%.

Various solvents may be used such as alkanes, among which mention may more particularly be made of hexane, heptane and isooctane; cycloalkanes, among which mention may be made by way of illustration of cyclohexane and cyclooctane; aromatic hydrocarbons, such as benzene, toluene and xylene; halogenated hydrocarbons; and mixtures of these solvents.

However, it should be noted that since the hydroperoxide is generally produced in the form of a solution in a hydrocarbon, for example cyclohexane, by oxidation of the latter, the decomposition reaction is advantageously carried out in a solution coming from the oxidation of the hydrocarbon (cyclohexane) in which the hydroperoxide concentration lies within the limits indicated above. This solution may be used as it stands or after certain constituents have been removed in a manner known per se. It is also possible to use a solution of hydroperoxide in the solvent, for example substantially pure cyclohexane.

The amount of catalyst involved may vary widely, especially depending on the conditions under which the process is carried out, namely a continuous, semi-continuous or batch process. In general, the amount of catalyst expressed as a molar percentage of active metal with respect to the hydroperoxide to be decomposed represents from 0.0001% to 20% and preferably from 0.01% to 10%.

Within the context of a continuous operation of the process, it is obvious that the amount of catalyst with respect to the hydroperoxide has no meaning and that the ratios indicated above may then be much higher.

The temperature is generally between 20 and 200° C. and preferably between 80 and 130° C.

Atmospheric pressure or pressure above atmospheric pressure will be sufficient to maintain the cyclohexane in the liquid phase.

The reaction time (or the residence time) is generally between a few minutes and 4 hours and can be adjusted in accordance with the production objectives, the amount of the various constituents of the catalytic system involved and the other parameters of the reaction.

At the end of reaction, the products may be recovered and/or separated by any suitable means, for example by distillation.

The hydroperoxides employed in the process of the invention are in general primary or secondary hydroperoxides derived from alkanes, cycloalkanes, aromatic alkyl hydrocarbons, the aromatic ring of which possibly has one or more substituents such as especially an alkyl group or a halogen atom, more particularly a chlorine atom, alkenes and cycloalkenes having from 3 to 20 carbon atoms.

As examples of such hydroperoxides, mention may be made of cyclohexyl hydroperoxide, cyclododecyl hydroperoxide, tetralin hydroperoxide, ethylbenzene hydroperoxide and pinane hydroperoxide.

Among these hydroperoxides, one of the more useful ones is very certainly cyclohexyl hydroperoxide, the oxidation of which results in cyclohexanol and cyclohexanone, these being intermediates in the preparation of adipic acid—one of the base compounds of nylon-6,6.

The examples below, given solely by way of indication, will illustrate the invention and its advantages and details.

EXAMPLE 1

Synthesis of Catalyst A (Ru/$ZrO_2$ Containing 5 wt % Ru)

The $ZrO_2$ support was precalcined for 2 hours at 500° C. After calcining, the zirconia (10 g) was placed in 500 ml of water and left at room temperature for 5 minutes with stirring. The pH of the solution was adjusted to pH 9 by addition of $Na_2CO_3$. The temperature was then raised while stirring the solution. An aqueous solution of $RuCl_3 \cdot nH_2O$, sold by STREM (about 20 ml for 1.79 g of $RuCl_3 \cdot nH_2O$) was then added at 90° C. over 20 minutes. The mixture was left for 15 minutes with stirring. The pH was then again adjusted to 8/9 by addition of $Na_2CO_3$ and the solution was stirred for 3 hours at 90° C.

Next, the mixture was cooled to 40-50° C. and then filtered. The cake was subjected to filtration-washing operations with water until a neutral pH of the washing water was obtained. The solid was dried for 18 hours at 120° C. and calcined at 400° C. for 2 hours.

EXAMPLE 2

Synthesis of Catalyst B (Ru/Y200 Acetylene Black Containing 5 wt % Ru)

The Y200 support (an acetylene black support sold by SN2A) was precalcined for 1 hour at 500° C. After calcining, the acetylene black (10 g) was placed in 500 ml of water and left for 5 minutes at room temperature with stirring. The pH of the solution was adjusted to pH 9 by addition of $Na_2CO_3$. The temperature was then raised while stirring the solution. An $RuCl_3$ solution in water (about 20 ml for 1.79 g of $RuCl_3$) was then added at 90° C. for 20 minutes. The mixture was left for 15 minutes, with stirring. The pH was again adjusted to 8/9 by addition of $Na_2CO_3$ and the solution was stirred for 3 hours at 90° C.

Next, the mixture was cooled to 40-50° C., and filtered. The cake was subjected to filtration-washing operations with water until a neutral pH of the washing water was obtained. The solid was dried for 18 hours at 120° C. and calcined at 400° C. for 2 hours.

EXAMPLE 3

Synthesis of Catalyst C (Ru/Y200 Acetylene Black Containing 5 wt % Ru)

The Y200 support was precalcined for 1 hour at 500° C. in air. After calcining, the acetylene black (10 g) was placed in 300 ml of THF and left for 30 minutes at room temperature with stirring. A solution of $Ru_3(CO)_{12}$ in tetrahydrofuran (THF) (about 100 ml for 1.12 g of $Ru_3(CO)_{12}$) was then added at room temperature over 30 minutes. The mixture was left for 30 minutes with stirring. The solution was then placed in a rotary evaporator for 4 hours (room temperature; atmospheric pressure; 200 rpm). The THF was, then evaporated under 20 mmHg. 11 g of solid were obtained.

EXAMPLE 4

Synthesis of Catalyst D (Ru/Alumina Containing 5 wt % Ru)

The alumina support, sold by Condea, was precalcined for 6 hours at 750° C. After calcining, the alumina (10 g) was placed in 500 ml of water and left for 5 minutes at room temperature with stirring. The pH of the solution was adjusted to pH 9 by addition of $Na_2CO_3$. The temperature was then raised (to 90° C. in 45 minutes) with stirring of the solution. A solution of $RuCl_3$ in water (about 20 ml for 1.98 g of $RuCl_3$) was then added at 90° C. over 20 minutes. The mixture was left for 15 minutes with stirring. The pH was again brought back to 8/9 by addition of $Na_2CO_3$ and the solution was stirred for 3 hours at 90° C.

Next, the mixture was cooled to 40-50° C., then filtered over a No. 4 glass frit. The cake was then taken up in 100 ml of water at 40-50° C. Four filtration-washing steps then followed until a neutral pH of the washing water was obtained. The solid was dried for 24 hours at 120° C. without calcining.

EXAMPLE 5

Synthesis of Catalyst E (Ru/La$_2$O$_3$ Containing 5 wt % Ru)

The lanthanum oxide support (sold by Rhodia) firstly underwent a pretreatment. This consisted in placing the lanthanum oxide in water (90 ml) for 30 minutes while the temperature was raised (to 90° C. over 3 hours). The solution was then cooled to 45° C., filtered, dried for 18 hours at 120° C. and then calcined at 400° C. for 24 h in air (5° C./min). After calcining, the lanthanum oxide (10 g) was placed in 500 ml of water and left for 5 minutes at room temperature with stirring. The pH of the solution was adjusted to pH 9 by addition of Na$_2$CO$_3$. The temperature of the solution was then raised (to 90° C. over 45 minutes) with stirring. A solution of RuCl$_3$ in water (about 20 ml for 1.08 g of RuCl$_3$) was then added at 90° C. over 20 minutes. The mixture was left for 15 minutes with stirring. The pH was again brought back to 8/9 by addition of Na$_2$CO$_3$ and the solution was stirred for 3 hours at 90° C.

Next, the mixture was cooled to 40-50° C., then filtered over a No. 4 glass frit. The cake was then taken up in 100 ml of water at 40-50° C. Four filtration-washing steps then followed until a neutral pH of the washing water was obtained. The solid was dried for 16 hours at 120° C. without calcining.

EXAMPLE 7

Synthesis of Catalyst F (Ru/Magnesia Containing 5 wt % Ru)

The magnesia support (UBE Industrie 100 Å) (10 g) firstly underwent a pretreatment. This consisted in placing the magnesia in water (100 ml) for 30 minutes while the temperature was raised (to 90° C. over 3 hours). The solution was then cooled to 45° C., filtered, dried for 16 hours at 120° C. in an oven, and then calcined at 400° C. for 24 h in air (5° C./min). The pretreated magnesia was placed in 400 ml of water and left for 5 minutes at room temperature with stirring. The pH of the solution was adjusted to pH 9 by addition of Na$_2$CO$_3$. The temperature of the solution was then raised (to 90° C. over 45 minutes) with stirring. A solution of RuCl$_3$ in water (about 20 ml for 1.08 g of RuCl$_3$) was then added at 90° C. over 20 minutes. The mixture was left for 15 minutes with stirring. The pH was again brought back to 8/9 by addition of Na$_2$CO$_3$ and the solution was stirred for 3 hours at 90° C.

Next, the mixture was cooled to 40-50° C. then filtered over a No. 4 glass frit. The cake was taken up in 100 ml of water at 40-50° C. Four filtration-washing steps then followed until a neutral pH of the washing water was obtained. The solid was dried for 16 hours at 120° C. without calcining.

EXAMPLE 8

Synthesis of Catalyst G (Ru/Magnesia Containing 5 wt % Ru)

The magnesia support (UBE Industrie 100 Å) (15 g) firstly underwent a pretreatment. This consisted in placing the magnesia in water (150 ml) for 30 minutes with the temperature being raised up to 90° C. over 3 hours. The solution was then cooled to 45° C., filtered, dried for 16 hours at 120° C. in an oven, then calcined at 400° C. for 24 h in air (5° C./min). The pretreated magnesia was placed in 150 ml of water and left for 10 minutes at room temperature with stirring. A solution of RuCl$_3$ in water (about 20 ml for 1.62 g of RuCl$_3$) was then added at room temperature over 15 minutes. The mixture was left for 1 hour 30 minutes at room temperature with stirring. After settling, the water was removed in a rotary evaporator under 20 mmHg at 50° C. The cake was oven dried for 16 hours at 120° C. 41 ml of 0.1M NaOH were then added to the cake so that the latter could be stirred. The solution obtained was then heated at 95° C. for 3 hours. 50 ml of 0.1M sodium hydroxide were then added and the solution was left to cool to 40-50° C. After two washings with 100 ml of water at 45° C., the solid was dried for 16 hours at 120° C. in an oven. Finally, the solid was taken up in 400 ml of water at room temperature, stirred for 30 minutes, heated at 70° C. for 3 hours and then centrifuged (pH of the aqueous phase=7) at 3500 rpm for 20 minutes. The solid thus obtained was dried for 16 hours at 120° C.

EXAMPLE 9

Synthesis of Catalyst H (Ru/Y70 Acetylene Black (SN2A) Containing 5 wt % Ru)

The SN2A Y70 acetylene black support (10 g) was firstly calcined for 1 hour at 500° C. The black (10 g) was placed in 400 ml of water and left for 5 minutes at room temperature with stirring. The pH of the solution was adjusted to pH 9 by addition of Na$_2$CO$_3$. The temperature of the solution was then raised (to 90° C. over 45 minutes) with stirring. A solution of RuCl$_3$ in water (about 20 ml for 1.08 g of RuCl$_3$) was then added at 90° C. over 20 minutes. The mixture was left for 15 minutes with stirring. The pH was again brought back to 8/9 by addition of Na$_2$CO$_3$ and the solution was stirred for 3 hours at 90° C.

Next, the mixture was cooled to 40-50° C., then filtered over a No. 4 glass frit. The cake was taken up in 100 ml of water at 40-50° C. Four filtration-washing steps then followed until a neutral pH of the washing water was obtained. The solid was dried for 16 hours at 120° C. without calcining.

EXAMPLE 10

Synthesis of Catalyst J (Ru/Ceria (HSA5) Containing 5 wt % Ru)

The HSA5 ceria support (sold by Rhodia) (10.2 g) was firstly calcined for 6 hours at 500° C. in air. The cerium oxide (10.2 g) was placed in 100 ml of water and a solution of anhydrous Ru(acac)$_3$ in acetone (about 100 ml for 2 g of Ru(acetylacetonate)$_3$) was then added at room temperature. The mixture was left for 2 hours at room temperature with stirring. The solution was concentrated in a rotary evaporator at 45° C., then dried for 16 hours in an oven at 120° C. 41 ml of 0.1M sodium hydroxide were then added to the dry cake and the solution was heated for 3 hours at 95° C. with stirring. Once the product had cooled to 40-50° C. it was filtered then washed 4 times at 45° C. with 100 ml of water. The solid was dried for 16 hours at 120° C. in an oven. The solid was then taken up in 210 ml of water at room temperature and then heated for 3 hours at 70° C. After cooling to 45° C., the solid was filtered, then dried for 16 hours at 120° C.

EXAMPLE 11

Synthesis of Catalyst K (Fe-Doped Ru on Y200 Acetylene Black)

The SN2A Y200 support (10 g) was calcined for 1 hour at 500° C. The acetylene black (10 g) was placed in 400 ml of water and stirred for 5 minutes. The mixture was gradually heated to 90° C. (over 45 minutes) and a solution of $FeCl_3.6H_2O$ (0.509 g in 50 ml of water) was added to the acetylene black at 90° C. over 13 minutes. The pH of the solution was brought to 5.5 by adding sodium bicarbonate. The solution was maintained for 30 minutes at 90° C. with stirring. After cooling to 45° C., four successive washing operations with 100 ml of water were carried out at 45° C. The product was dried for 16 hours at 120° C. in an oven. The solid was then placed in the reactor in the presence of 400 ml of water, then heated to 90° C. and the pH was adjusted to 10 with $Na_2CO_3$. Stirring was maintained for 1 hour at 90° C. A solution of alpha-$RuCl_3$ in water (about 20 ml for 1.08 g of $RuCl_3$) was then added at 90° C. over 20 minutes. The mixture was left for 3 hours at 90° C. with stirring. Once the product had cooled to 40-50° C., it was filtered, then washed and filtered 4 times in succession so as to obtain a neutral pH of the washing water. The solid was dried for 16 hours at 120° C. in an oven.

EXAMPLE 12

Synthesis of Catalyst L (Co-Doped Ru on Y200 Acetylene Black)

The SN2A Y200 support (10 g) was calcined for 1 hour at 500° C. The acetylene black (10 g) was placed in 400 ml of water and stirred for 5 minutes. The mixture was gradually heated to 90° C. (over 45 minutes) and sodium bicarbonate added so as to reach a pH of 10. A solution of alpha-$RuCl_3$ in water (about 20 ml for 1.08 g of $RuCl_3$) was then added over 20 minutes at 90° C. The mixture was left for 1 hour at 90° C. with stirring. A solution of $CoCl_2.6H_2O$ (1.429 g in 20 ml of water) was then added to the reactor at 90° C. The solution was maintained for 1 hour at 90° C. with stirring. After cooling to 45° C. the solid was filtered over a No. 4 glass frit. The cake was taken up in 100 ml of water at 40-50° C. and four successive washing operations were carried out so as to obtain a neutral pH of washing water. The solid was dried for 16 hours at 120° C. in an oven.

EXAMPLES 13 to 24

Catalytic Results in CHHPO Deperoxidation

The supported catalysts were tested under conventional deperoxidation conditions: 40 g of oxidate (coming from the self-oxidation of cyclohexane (5% CHHPO, as described in Patent FR2087375) were brought into contact with about 170 mg of heterogeneous catalyst for several hours at 80° C. in a reactor on which a Dean Stark apparatus was fitted (for continuous removal of the water formed in the reaction mixture). The catalysts (containing 5 wt % Ru) were used with Ru/CHHPO molar ratios of 0.5%. The residual CHHPO concentrations were measured by potentiometric back titration (iodine/thiosulphate) and the cyclohexanol (CHol) and cyclohexanone (CHone) concentrations were measured by GC. The results are given in the table below. DC (degree of conversion) is understood to mean the ratio of the number of moles of CHHPO converted to the initial number of moles of CHHPO.

| Example | Cata No. | Metal | Support | t (min) | DC (%) | CHone/ CHol |
|---|---|---|---|---|---|---|
| Example 13 | A | Ru | Zirconia | 60 | 97.4 | / |
| Example 14 | B | Ru | Y200 acetylene black | 50 | 97.7 | 0.52 |
| Example 15 | C | Ru | Y200 acetylene black | 60 | 97.3 | 0.55 |
| Example 16 | D | Ru | Alumina | 90 | 97.1 | 0.52 |
| Example 17 | E | Ru | Lanthanum Oxide | 60 | 97.7 | 0.52 |
| Example 19 | F | Ru | Magnesia | 270 | 97.8 | 0.53 |
| Example 20 | G | Ru | Magnesia | 300 | 95.3 | 0.53 |
| Example 21 | H | Ru | Y70 acetylene black | 110 | 93.5 | 0.48 |
| Example 22 | J | Ru | Ceria | 45 | 97.9 | 0.63 |
| Example 23 | K | Ru/Fe | Y200 acetylene black | 90 | 95.8 | 0.48 |
| Example 24 | L | Ru/Co | Y200 acetylene black | 120 | 94.5 | 0.47 |

The invention claimed is:

1. A process for decomposing organic hydroperoxides, comprising the step of carrying out a decomposition reaction in the presence of a catalyst into alcohols and ketones, said catalyst consisting essentially of at least one ruthenium-based catalytically active metallic element incorporated into a support comprising carbon black obtained by pyrolysis of organic compounds; and at least one doping element selected from the group consisting of a rare-earth metal, titanium, zirconium, vanadium, niobium, tantalum, molybdenum, tungsten, manganese, rhenium, iron, cobalt, nickel, rhodium, palladium, platinum, gold, silver, copper, iridium and osmium.

2. The process according to claim 1, wherein the support has a high specific surface area.

3. The process according to claim 1, wherein the catalyst is present in an amount expressed as a molar percentage of ruthenium with respect to the number of moles of hydroperoxide to be decomposed, from 0.0001% to 20%.

4. The process according to claim 1, wherein the decomposition reaction is carried out at a temperature of between 20° C. and 200° C.

5. The process according to claim 1, wherein the reaction is carried out in a solution of the hydroperoxide in a solvent.

6. The process according to claim 5, wherein the solvent is a hydrocarbon, an alkane, or a halogenated hydrocarbon.

7. The process according to claim 6, wherein the solvent is a hydrocarbon identical to that whose oxidation leads to the hydroperoxide to be decomposed.

8. The process according to claim 5, wherein the hydroperoxide has a concentration of between 1% and 80% by weight with respect to the weight of the solution.

9. The process according to claim 1, wherein the hydroperoxide is a primary or secondary hydroperoxides derived from alkanes, cycloalkanes, aromatic alkyl hydrocarbons, alkenes or cycloalkenes having from 3 to 20 carbon atoms.

10. The process according to claim 9, wherein the aromatic alkyl hydrocarbons have one or more substituents which are alkyl groups or halogen atoms.

11. The process according to claim 9, wherein the hydroperoxide is cyclohexyl hydroperoxide, cyclododecyl hydroperoxide, tetralin hydroperoxide, ethylbenzene hydroperoxide or pinane hydroperoxide.

* * * * *

UNITED STATES PATENT AND TRADEMARK OFFICE
CERTIFICATE OF CORRECTION

| | | |
|---|---|---|
| PATENT NO. | : 7,396,961 B2 | Page 1 of 1 |
| APPLICATION NO. | : 11/336008 | |
| DATED | : July 8, 2008 | |
| INVENTOR(S) | : Didier Bonnet et al. | |

It is certified that error appears in the above-identified patent and that said Letters Patent is hereby corrected as shown below:

On the Title page, the Related U.S. Application Data section is incomplete:

It should read:

--Related U.S. Application Data

(63)  Continuation of application No. 10/493,876, filed on Aug. 18, 2004, now abandoned, which is a 371 of PCT/FR02/03713, filed on Oct. 29, 2002.--

On the Title page, the Foreign Application Priority Data section is missing:

It should read:

--(30) Foreign Application Priority Data

Oct. 30, 2001 (FR) ........................01 14038--

Signed and Sealed this
Fifteenth Day of December, 2015

Michelle K. Lee
*Director of the United States Patent and Trademark Office*